United States Patent
Wimmer, IV (10) Patent No.: US 12,336,605 B1
(45) Date of Patent: Jun. 24, 2025

(54) IDENTIFICATION BRACELET

(71) Applicant: Road ID, Inc., Covington, KY (US)

(72) Inventor: Edward Michael Wimmer, IV, Lakeside Park, KY (US)

(73) Assignee: Road ID, Inc., Covington, KY (US)

(*) Notice: Subject to any disclaimer, the term of this patent is extended or adjusted under 35 U.S.C. 154(b) by 0 days.

(21) Appl. No.: 18/426,525

(22) Filed: Jan. 30, 2024

Related U.S. Application Data (60) Provisional application No. 63/613,143, filed on Dec. 21, 2023.

(51) Int. Cl.
| | |
|---|---|
| *A44C 5/20* | (2006.01) |
| *A44C 5/00* | (2006.01) |
| *A44C 5/14* | (2006.01) |
| *A61B 90/94* | (2016.01) |

(52) U.S. Cl.
CPC ............. *A44C 5/14* (2013.01); *A44C 5/0015* (2013.01); *A44C 5/0053* (2013.01); *A61B 90/94* (2016.02)

(58) Field of Classification Search
CPC ....... A44C 5/14; A44C 5/0015; A44C 5/0053; A44C 5/18; A44C 5/185; A44C 5/20; A44C 5/2071; A44C 5/208; A61B 90/94; Y10T 24/45063; Y10T 24/45042; Y10T 24/4782; Y10T 24/3423; Y10T 24/3653; Y10T 24/47; H04B 1/385
USPC ....................................... 63/3.1, 3.2
See application file for complete search history.

(56) References Cited

U.S. PATENT DOCUMENTS

| | | | | |
|---|---|---|---|---|
| 4,154,011 A | * | 5/1979 | Rakestraw | G09F 3/005 |
| | | | | 292/307 A |
| 2008/0005875 A1 | * | 1/2008 | Friedman | H04B 1/385 |
| | | | | 24/578.15 |
| 2020/0110439 A1 | * | 4/2020 | Deng | H04R 1/1041 |

* cited by examiner

*Primary Examiner* — Jack W Lavinder
(74) *Attorney, Agent, or Firm* — Sand, Sebolt & Wernow Co., LPA (57) ABSTRACT

An identification bracelet having a locking mechanism. The locking mechanism having a screw and a receiver where the receiver is connected with a body of the bracelet. The screw is connected with one of a plurality of screw holes on the body of the bracelet which determine a diameter of the bracelet. The screw is connected with the receiver where the screw tightens within the receiver and secures the bracelet onto a part of a body by an external tool. Once secured, the bracelet is not easily removable and may only be removed by use of the external tool.

20 Claims, 10 Drawing Sheets

IDENTIFICATION BRACELET

REFERENCE TO RELATED APPLICATIONS

This application claims the benefit of U.S. Provisional Application Ser. No. 63/613,143, filed on Dec. 21, 2023; the disclosure of which is incorporated herein by reference.

TECHNICAL FIELD

The present disclosure relates generally to an identification bracelet. More particularly, the present disclosure relates to an identification bracelet with a locking mechanism. Specifically, the present disclosure relates to an adjustable identification bracelet with a locking mechanism.

BACKGROUND ART

Bracelets are commonly worn by many people throughout the world. Often these bracelets are easily removable with a clasp to take the bracelet on and off at will. Bracelet are worn for a variety of reasons such as fashion, but for many people bracelets are worn for a more utilitarian reason. Bracelets with identification or medical information can be vital for the health of the wearer.

People of all ages have reasons to need to wear a bracelet with personal information. Some people, such as children or people with intellectual or physical disabilities will routinely try to remove the bracelet with the vital identification or medical information. Therefore, it is advantageous to have a bracelet that cannot be easily removed by the wearer.

SUMMARY OF THE INVENTION

An identification bracelet is disclosed herein. The identification bracelet having a locking mechanism. The locking mechanism having a screw and a receiver where the receiver is connected with a body of the bracelet. The screw is connected with one of a plurality of screw holes on the body of the bracelet which determine a diameter of the bracelet. The screw is connected with the receiver where the screw tightens within the receiver and secures the bracelet onto a part of a body by an external tool. Once secured, the bracelet is not easily removable and may only be removed by use of the external tool.

In one aspect, an exemplary embodiment of the present disclosure may provide an identification bracelet, said bracelet comprising: a body having a first end and a second end opposite to the first end; a receiver hole defined in the body at the first end; a plurality of screw holes defined in the body at a location between the first end and the second end and is remote from the receiver hole; and a locking mechanism fixedly engaged with the body at the receiver hole and selectively operably engageable with the body at a selected hole of the plurality of screw holes.

This exemplary embodiment or another exemplary embodiment may further include the bracelet wherein the body of the bracelet comprises: an outer surface and an inner surface opposite to the outer surface; an indicia on the outer surface of the body of the bracelet; and wherein the indicia includes at least one of health information, personal information, contact information and combinations thereof. This exemplary embodiment or another exemplary embodiment may further include the bracelet wherein the body of the bracelet comprises: a bore defined at the second end; and wherein the bore is configured to receive the first end of the body. This exemplary embodiment or another exemplary embodiment may further include the bracelet wherein the locking mechanism comprises: a screw selectively operably engageable with the body at the selected hole of the plurality of screw holes; and a receiver fixedly engaged with the body at the receiver hole and is configured to receive the screw. This exemplary embodiment or another exemplary embodiment may further include the bracelet wherein the screw comprises: a first flange selectively operably engageable with an outer surface of the body; a first shaft operably engaged with the first flange and is selectively operably engageable with an inner wall of the selected hole of the plurality of screw holes; and a second flange operably engaged with the first shaft and is selectively operably engageable an inner surface of the body. This exemplary embodiment or another exemplary embodiment may further include the bracelet wherein the screw further comprises: a second shaft operably engaged with the second flange and is selectively operably engageable with the receiver; an socket defined in the first flange and the first shaft; and wherein the socket is adapted to receive an external tool for securing the screw with the receiver. This exemplary embodiment or another exemplary embodiment may further include the bracelet wherein the external tool is a hex key. This exemplary embodiment or another exemplary embodiment may further include the bracelet wherein the body of the bracelet further comprises: an outer surface and an inner surface opposite one another; a first side and a second side opposite one another and positioned between the outer surface and the inner surface; and wherein each of the receiver hole and the plurality of screw holes extends through the outer surface and the inner surface. This exemplary embodiment or another exemplary embodiment may further include the bracelet wherein the receiver comprises: a first portion and a second portion configured to engage with one another; and wherein the first portion and the second portion are configured to fixedly engage with the body of the bracelet inside of the receiver hole. This exemplary embodiment or another exemplary embodiment may further include the bracelet wherein the receiver comprises: a first portion comprising: a first member operably engaged with an outer surface of the body; a second member integrally engaged with the first member and is operably engaged with the receiver hole of the body; a first passage extending between the first member and the second member; a second portion comprising: a third member operably engaged with to an inner surface of the body; a fourth member integrally engaged with the third member and is configured to be received within the receiver hole of the body; a second passage extending between the third member and the fourth member; a plurality of tines extending outwardly from the third member and engaged with the third member; wherein the fourth member of the second portion is configured to be received within first passage of the first portion; and wherein the second passage is configured to receive the screw. This exemplary embodiment or another exemplary embodiment may further include the bracelet wherein the first portion and the second portion define outer diameters substantially equal to one another. This exemplary embodiment or another exemplary embodiment may further include the bracelet wherein a wall of the fourth member of the second portion is contiguous with the first passage of the first portion. This exemplary embodiment or another exemplary embodiment may further include the bracelet wherein a top surface of the fourth member of the second member is substantially aligned with a top surface of the first member of the first portion. This exemplary embodiment or another exemplary embodiment may further include the bracelet wherein a tip of each of the plurality of tines is contiguous with a bottom surface of the first member of the first portion of the receiver. This exemplary embodiment or another exemplary embodiment may further include the bracelet wherein the receiver further comprises the second passage configured to receive a second shaft of the screw; and wherein the second passage of the second portion and the second shaft of the screw are threaded.

In one aspect, an exemplary embodiment of the present disclosure may provide a method of securing an identification bracelet to an extremity of a wearer, comprising steps of: placing a body of the bracelet around the extremity of the wearer; inserting a first end of the body of the bracelet into a bore of the body; guiding a receiver of a locking mechanism along an inner surface of the body of the bracelet; aligning the receiver with a screw of the locking mechanism; tightening the screw into the receiver; and securing the bracelet to the extremity of the wearer.

This exemplary embodiment or another exemplary embodiment may further include the method further comprising steps of: wrapping the body of the bracelet about the extremity of the wearer; determining a second inner diameter of the body of the bracelet that substantially matches with an outer diameter of the extremity; selecting a desired hole of the plurality of screw holes that sets the second inner diameter of the body; and placing the screw into the desired hole of the plurality of screw holes. This exemplary embodiment or another exemplary embodiment may further include the method wherein the step of tightening the screw into the receiver further includes that the screw is tightened into the receiver with an external tool separate from the bracelet.

In one aspect, an exemplary embodiment of the present disclosure may provide A method for protecting an at risk individual, comprising the steps of: placing a bracelet around an extremity of the at risk individual; securing the bracelet with a locking mechanism so that the bracelet cannot be removed without an external tool; and putting indicia on the bracelet relating to the at risk individual wearing the bracelet.

This exemplary embodiment or another exemplary embodiment may further include the method wherein the indicia on an outer surface of the bracelet, and wherein the indicia includes at least one of health information, personal information, contact information and combinations thereof.

BRIEF DESCRIPTION OF THE DRAWINGS

Sample embodiments of the present disclosure are set forth in the following description, are shown in the drawings and are particularly and distinctly pointed out and set forth in the appended claims.

Similar numbers refer to similar parts throughout the drawings.

DETAILED DESCRIPTION

Figure 1:
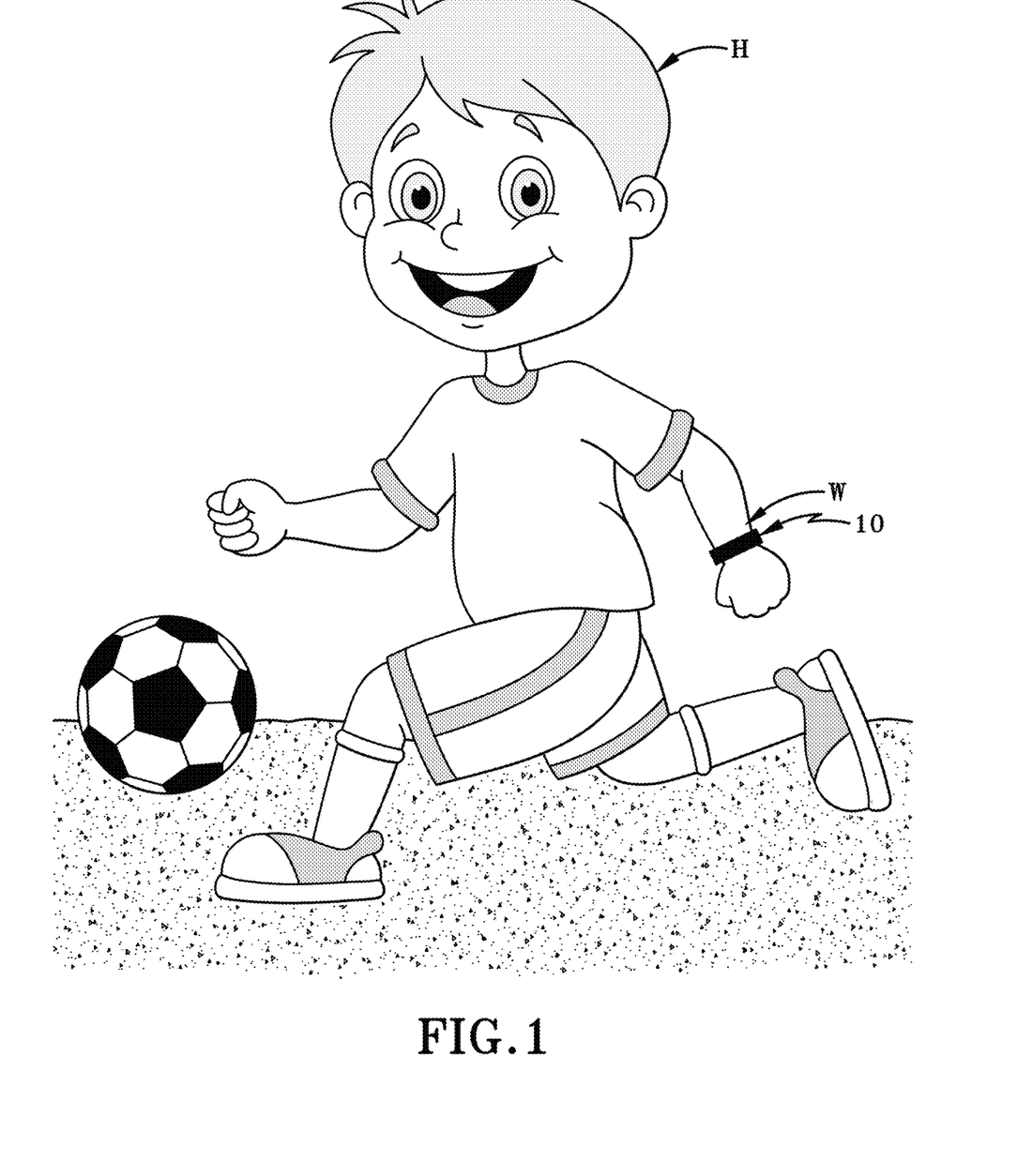
FIG. 1 (FIG. 1) is an environmental view of an identification bracelet in accordance with the present disclosure, wherein the identification bracelet is placed on a wrist of a human.
Figure 2:
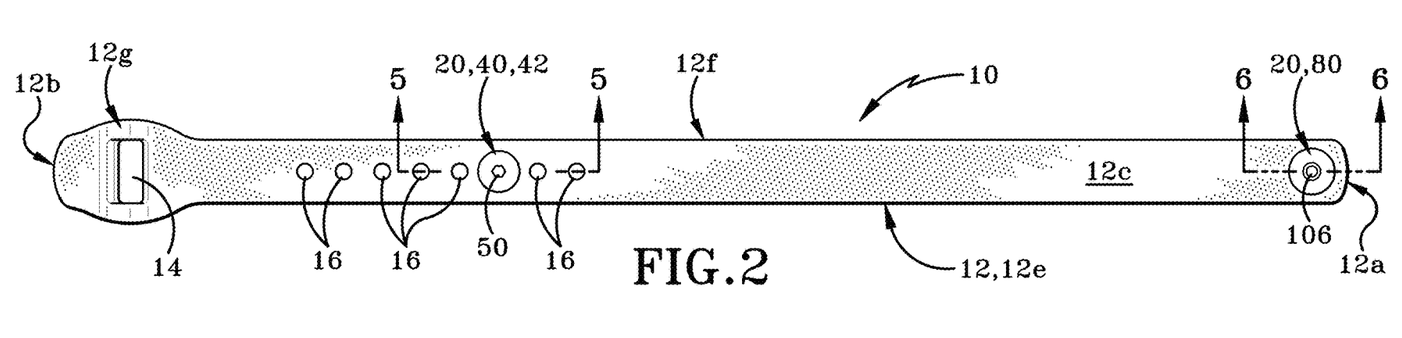
FIG. 2 (FIG. 2) is a top plan view of the bracelet in accordance with the present disclosure and shown in FIG. 1.
Figure 3:
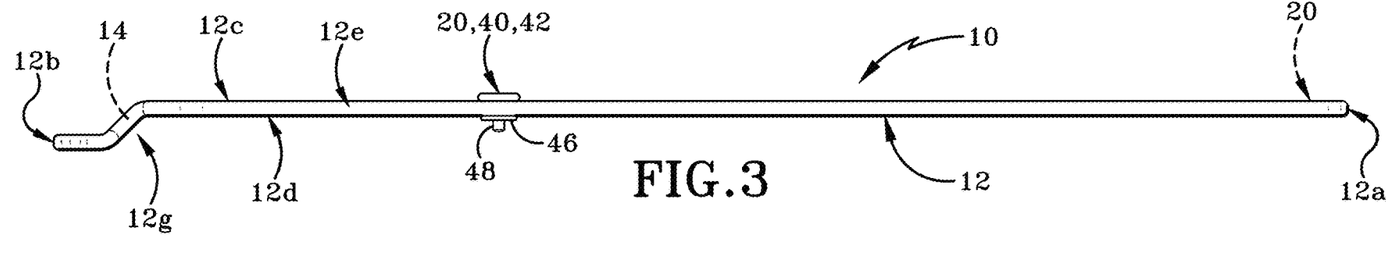
FIG. 3 (FIG. 3) is a side elevation view of the bracelet shown in FIG. 2.
Figure 4:
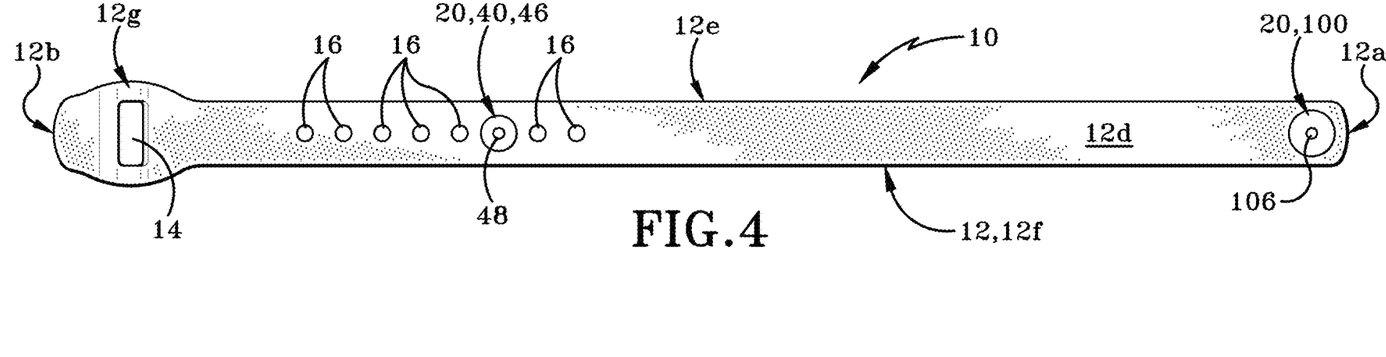
FIG. 4 (FIG. 4) is a bottom plan view of the bracelet shown in FIG. 2.
Figure 5:
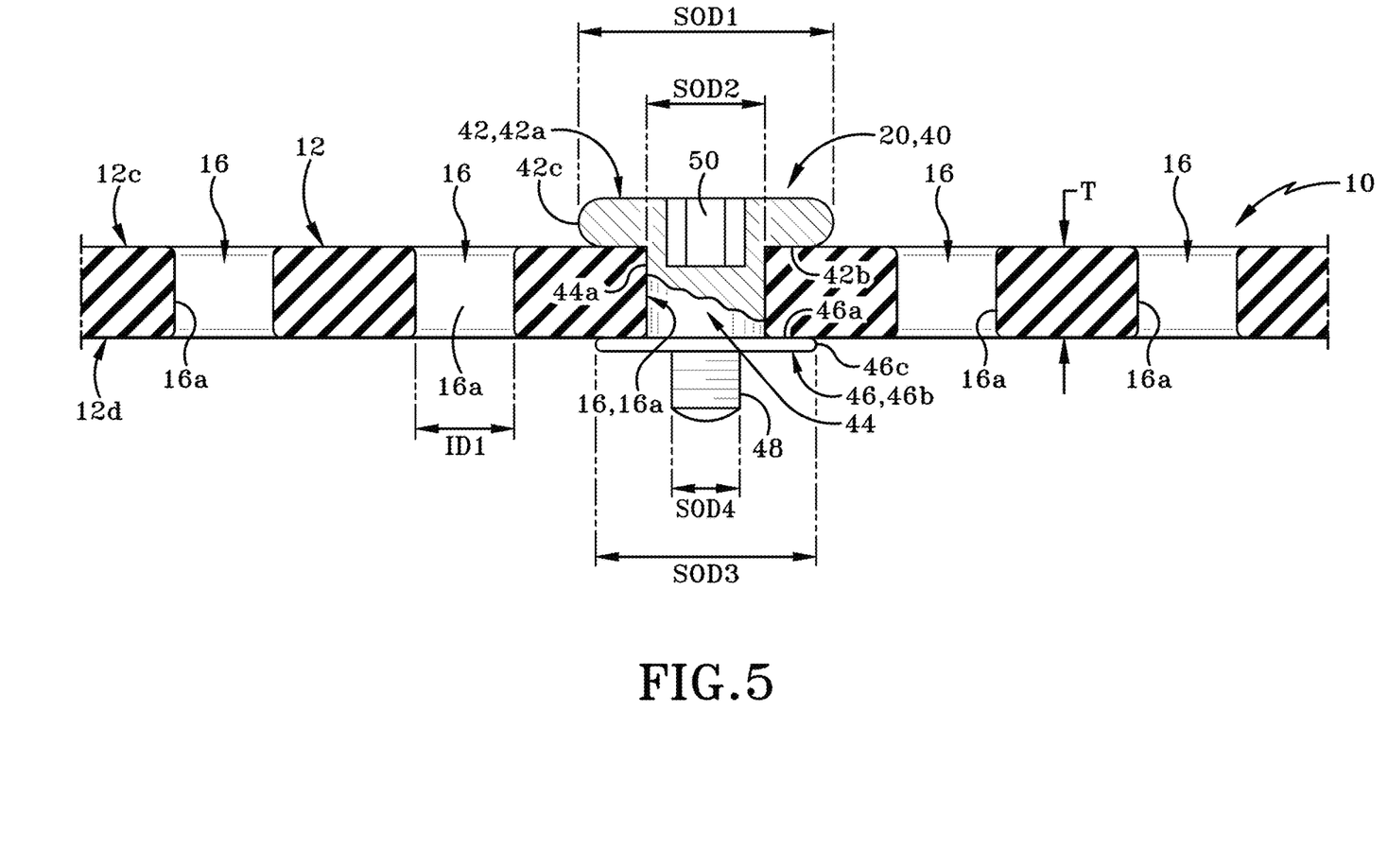
FIG. 5 (FIG. 5) is a sectional view of the bracelet take along and looking in the direction of line 5-5 of FIG. 2.

FIG. 1 shows a human "H" playing ball with an identification bracelet 10 placed on the human's "H" wrist "W". Referring now to FIGS. 2-4, bracelet 10 includes a body 12. The body 12 is adapted to receive a plate wherein text information, such as identification or medical information, may be placed. The body 12 includes a first end 12a and a second end 12b opposite and substantially parallel to the first end 12a. The body 12 further includes an outer surface 12c and an inner surface 12d opposite the outer surface 12c. The body 12 even further includes a first side 12e and a second side 12f opposite and substantially parallel to the first side 12e. Referring now to FIG. 5, body 12 is of a thickness "T" defines as the distance between outer surface 12c and inner surface 12d. The body 12 may be made of a flexible material such as rubber. It should be understood that any material may be suitable for the body 12 that would allow the body 12 to be flexible around a portion of a human's body. It should be understood that bracelet 10 may be flexible around a portion of a body other than a human's such as an animal.

In one specific embodiment, body 12 may further comprise an indicia on the outer surface 12c of the body 12. The identifier may comprise information such as health information, personal information, contact information or any combination thereof.

Referring to FIG. 3, the body 12 may include a stepped section 12g where a rectangular bore 14 is disposed. The stepped section 12g may extend downwardly from a location between the first end 12a and the second end 12b and towards the second end 12b such that the second end 12b is positioned below the first end 12a when viewed from a side elevation view (see FIG. 3). Rectangular bore 14 is defined by extending through the body 12 from outer surface 12c towards inner surface 12d. Rectangular bore 14 is configured to receive the first end 12a where the outer surface 12c near the first end 12a touches the inner surface 12d near the second end 12b.

Body 12 further defines a plurality of screw holes 16. As best seen in FIG. 2, the plurality of screw holes 16 is disposed closer to the second end 12b than the first end 12a. The plurality of screw holes 16 also extends through the body 12 from outer surface 12c to inner surface 12d such that the outer surface 12c and the inner surface 12d are in operative communication with one another at each hole of the plurality of screw holes 16. The plurality of screw holes 16 further define an inner wall 16a extending between outer surface 12c and inner surface 12d. Each of the plurality of screw holes 16 further define a first inner diameter "ID1" extending along the length of each of the plurality of screw holes 16. Referring now to FIG. 6A, body 12 further defines a receiver hole 18 disposed near the first end 12a. In the present disclosure, the receiver hole 18 extends through the body 12 from the outer surface 12c towards the inner surface 12d such that the outer surface 12c and the inner surface 12d are in operative communication with one another at the receiver hole 18. The plurality of screw holes 16 is remote the receiver hole 18.

Figure 6:
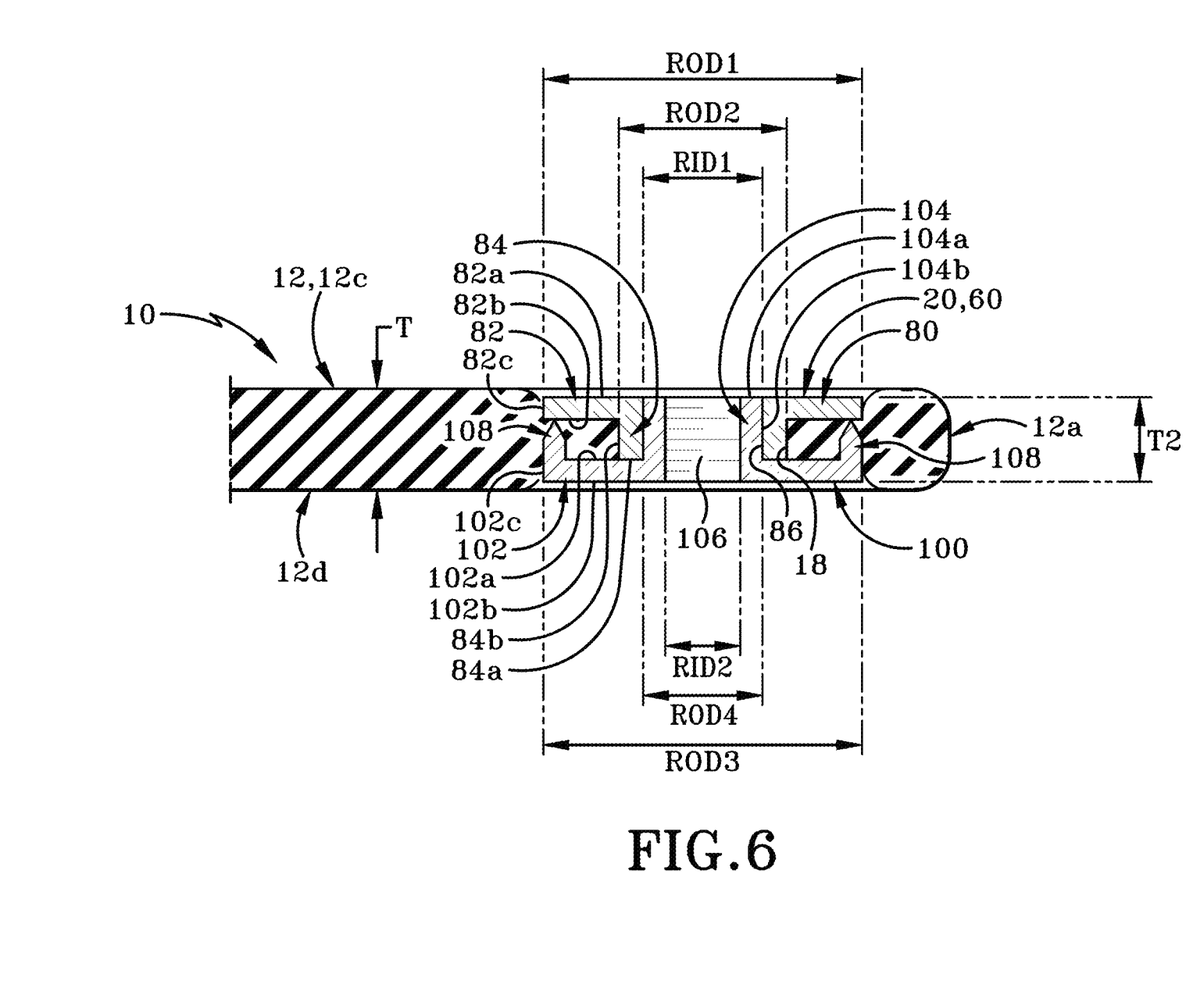
FIG. 6 (FIG. 6) is a sectional view of the bracelet take along and looking in the direction of line 6-6 of FIG. 2.
Figure 6A:
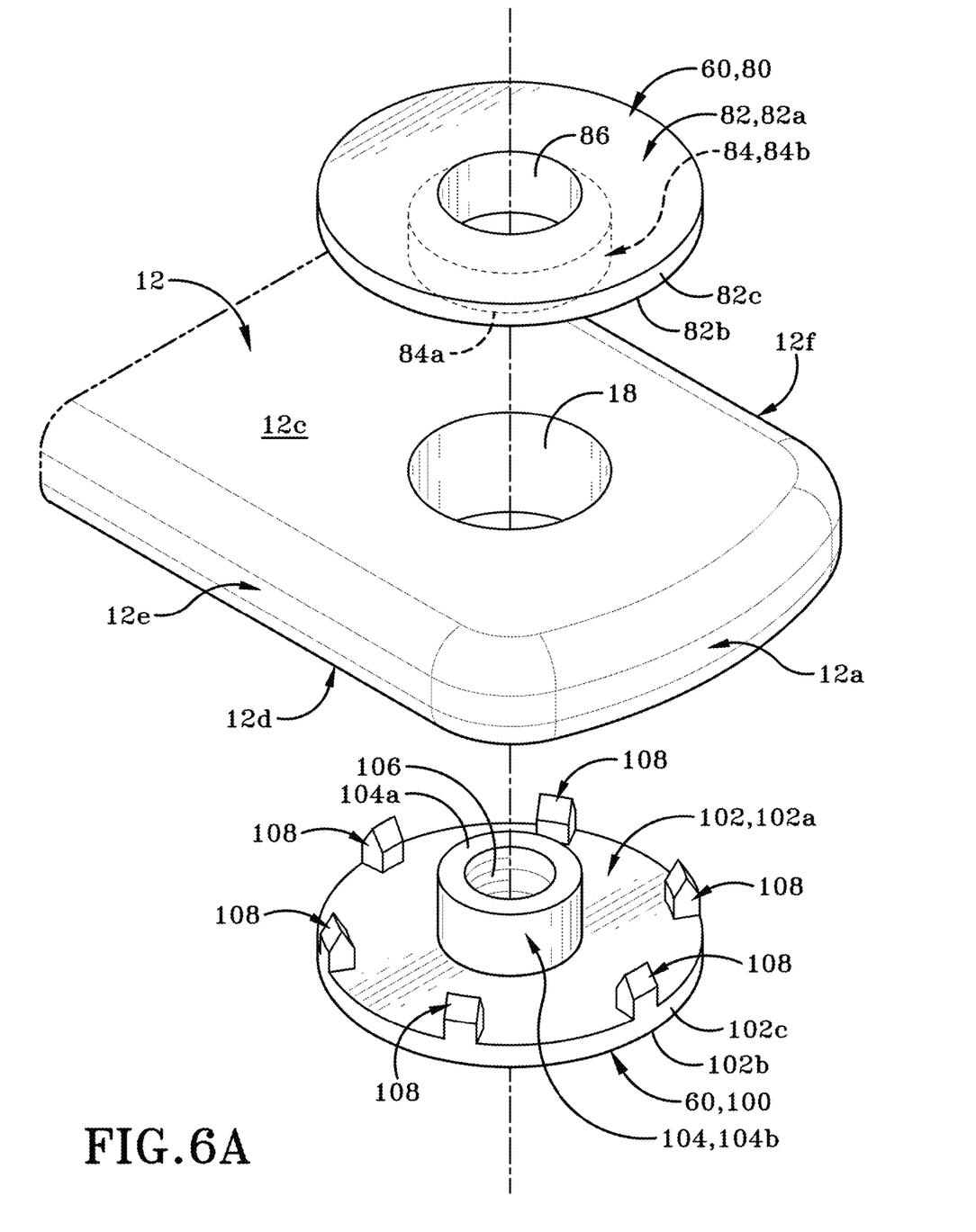
FIG. 6A (FIG. 6A) is a partial exploded view of a portion of the bracelet, a first portion of a receiver of a locking mechanism, and a second portion of the receiver of the locking mechanism shown in FIG. 2.
Figure 6B:
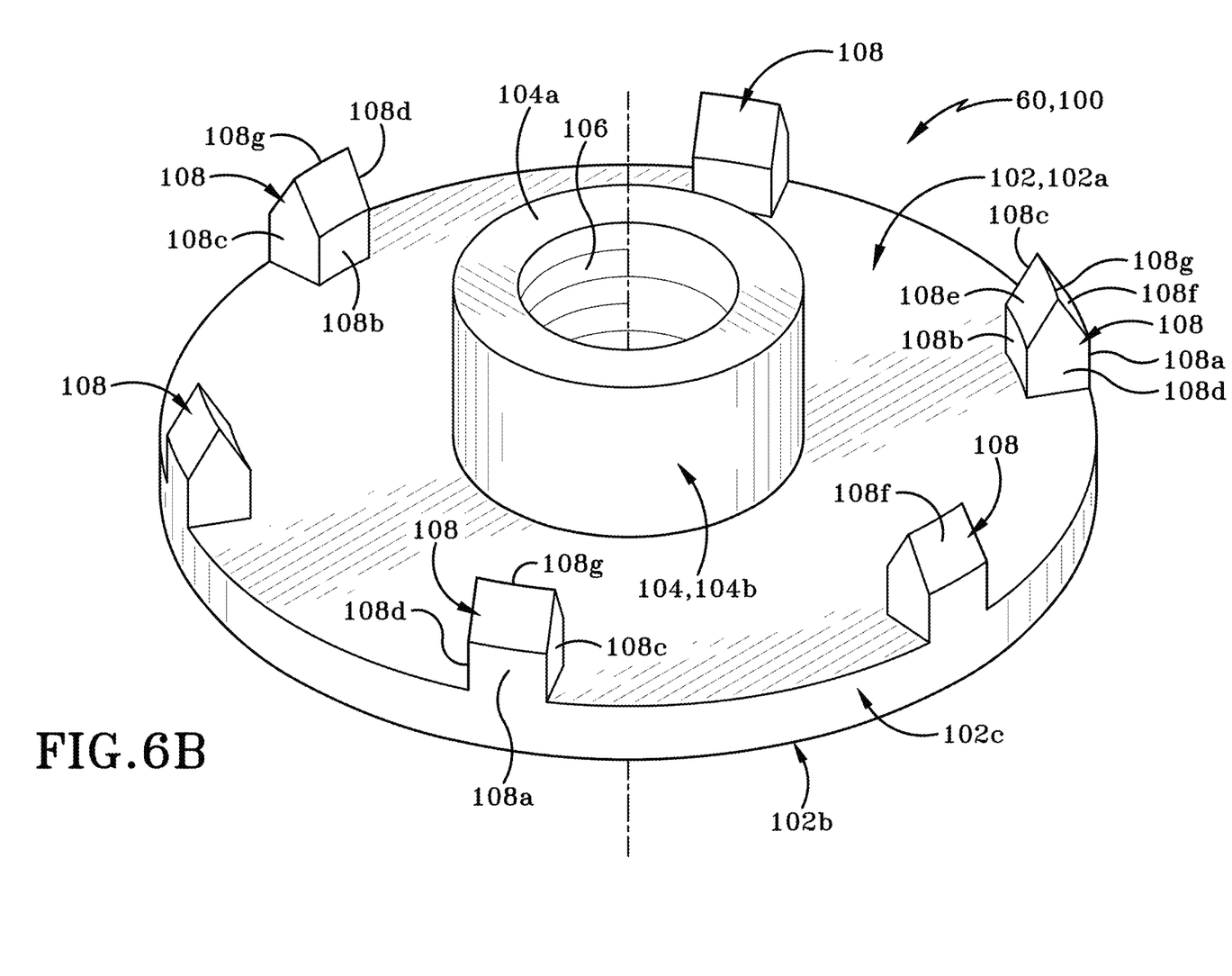
FIG. 6B (FIG. 6B) is a front, left, top isometric perspective view the second member of the receiver shown in FIG. 6A.

Referring now to FIGS. 5-6B, bracelet 10 includes a locking mechanism 20 that is selectively operatively engageable with the body 12. Locking mechanism 20 has a screw 40 and a receiver 60 for setting a desired extremity diameter of the body 12 dependent upon a wearer's extremity diameter. In one exemplary embodiment, screw 40 and receiver 60 may be generally circular in shape when viewed from a top plan view (see FIG. 2) or a bottom plan view (see FIG. 4). In other exemplary embodiments, screw 40 and receiver 60 may define a suitable shape necessary and/or desired for setting a desired extremity diameter of the body 12 dependent upon a wearer's extremity diameter.

Referring to FIG. 5, screw 40 includes a first flange 42 and a first shaft 44 continuous with one another and selectively operably engageable with body 12 at the plurality of screw holes 16. First flange 42 is selectively operably engageable with outer surface 12c of the body. First shaft 44 is selectively operably engageable with an inner wall 16a of the plurality of screw holes 16. First flange 42 includes a top surface 42a and a bottom surface 42b opposite and substantially parallel to one another. First flange 42 further includes a peripheral edge 42c that extends vertically between the top surface 42a and bottom surface 42b of first flange 42. First flange 42 defines a first screw outer diameter "SOD1." First shaft 44 defines a second screw outer diameter "SOD2" that is continuous along the length of first shaft 44.

Screw 40 further includes a second flange 46 and a second shaft 48 continuous with one another and selectively operably engageable with the body at the plurality of screw holes 16. Second flange 46 is selectively operably engageable with the inner surface 12d of the body 12. Second shaft 48 is selectively operably engageable with the receiver 60 of the locking mechanism 20. In the present disclosure, the second flange 46 also is continuous with first shaft 44. Second flange 46 includes a top surface 46a and a bottom surface 46b opposite and substantially parallel to one another. Second flange 46 further includes a peripheral edge 46c that extends vertically between the top surface 46a and bottom surface 46b of second flange 46. Second flange 46 defines a third screw outer diameter "SOD3." Second shaft 48 also defines a fourth screw outer diameter "SOD4" that is continuous along the length of second shaft 48. Screw 40 defines a socket 50 that extends from the top surface 42a of the first flange 42 toward the second flange 46. In one specific embodiment, second shaft 48 may be a threaded shaft. Further in this embodiment, the socket 50 may be adapted to receive an external tool for manipulating and/or rotating the screw 40 for attachment operations, which is discussed in greater detail below. In yet another specific embodiment, the external tool may be a hex key.

Referring to FIG. 5, screw 40 selectively engages any one of the plurality of screw holes 16. Specifically, screw 40 may be placed within one of the plurality of screw holes 16 to a set a desired diameter of the bracelet 10 when secured to a wearer's extremity. Once screw 40 is placed within the plurality of screw holes 16, the bottom surface 42b of the first flange 42 is contiguous with outer surface 12c of the body 12. Further, once screw 40 is placed within the plurality of screw holes 16, an outer surface 44a of first shaft 44 is contiguous with an inner wall 16a of the body 12 defining the selected hole of the plurality of screw holes 16. Even further, once screw 40 is placed within the plurality of screw holes 16, the top surface 46a of second flange 46 is contiguous with inner surface 12d of body 12. First screw outer diameter "SOD1" of first flange 42 is substantially greater than first inner diameter "ID1" of each of the plurality of screw holes 16. Second outer screw diameter "SOD2" of the first shaft 44 is substantially equal to and corresponds with the first inner diameter "ID1" of each of the plurality of screw holes 16. Third outer screw diameter "SOD3" of second flange 46 is substantially greater than first inner diameter "ID1" of each of the plurality of screw holes 16. The first screw outer diameter "SDO1" of first flange 42 and third screw outer diameter "SOD3" of second flange 46 being larger than first inner diameter "ID1" of each of the plurality of screw holes 16 allows for the screw 40 to be secured within one of the plurality of screw holes 16 and. Even further, a length of first shaft 44 of screw 40 is substantially equal to the thickness "T" of body 12 of bracelet 10.

Referring now to FIGS. 6, 6A, and 6B, receiver 60 of locking mechanism 20 includes a first portion 80 and second portion 100 configured to fixedly engage with body 12 of the bracelet 10 at receiver hole 18. First portion 80 includes a first member 82 and second member 84 continuous with one another. First member 82 includes a top surface 82a and a bottom surface 82b opposite and substantially parallel to one another. First member 82 further includes a peripheral edge 82c that extends vertically between the top surface 82a and the bottom surface 82b. The peripheral edge 82c may also be continuous with and substantially perpendicular to top surface 82a and bottom surface 82b. Peripheral edge 82c also defines a first receiver outer diameter "ROD1" of first member 82 (FIG. 6).

Referring to FIGS. 6 and 6A, second member 84 extends from the first member 82. Particularly, the second member 84 extends vertically downward from the bottom surface 82b of the first member 82 and ends at a bottom surface 84a of second member 84. Bottom surface 84a is opposite to and substantially parallel to top surface 82a and bottom surface 82b of first member 82. Second member 84 further includes an outer surface 84b that extends vertically between the bottom surface 82b of first member 82 and bottom surface 84a of second member 84. Outer surface 84b may also be continuous with and substantially perpendicular to bottom surface 82b of first member 82 and bottom surface 84a of second member 84. In the present disclosure, a second receiver outer diameter "ROD2" is also defined along an entire length of the second member 84 (FIG. 5); first receiver outer diameter "ROD1" of first member 82 is greater than second receiver outer diameter "ROD2" of second member 84 (FIG. 6).

First portion 80 further defines a first passage 86 extending through the first member 82 and second member 84.

Specifically, first passage 86 extends from top surface 82a of first member 82 through the second member 84. The first member 82 and the second member 84 collectively define a first receiver inner diameter "RID1" for first passage 86 (FIG. 6).

Still referring to FIGS. 6, 6A, and 6B, second portion 100 includes a third member 102 and fourth member 104 continuous with one another. Third member 102 includes a top surface 102a and a bottom surface 102b opposite and substantially parallel to one another. Third member 102 further includes a peripheral edge 102c that extends vertically between the top surface 102a and the bottom surface 102b. The peripheral edge 102c may also be continuous with and substantially perpendicular to top surface 102a and bottom surface 102b. Peripheral edge 102c also defines a third receiver outer diameter "ROD3" of third member 102 (FIG. 6).

Referring to FIGS. 6A and 6B, fourth member 104 extends from the third member 102. Particularly, the fourth member 104 extends vertically upward from the bottom surface 102b of the third member 102 and ends at a top surface 104a of fourth member 104. Top surface 104a is opposite to and substantially parallel to top surface 102a and bottom surface 102b of third member 102. Fourth member 104 further includes an outer surface 104b that extends vertically between top surface 104a of third member 102 and top surface 104a of fourth member 104. Top surface 104a may also be continuous with and substantially perpendicular to top surface 102a of third member 102 and top surface 104a of fourth member 104. In the present disclosure, a fourth receiver outer diameter "ROD4" is also defined along an entire length of the fourth member 104 (FIG. 5); third receiver outer diameter "ROD3" of third member 102 is greater than fourth receiver outer diameter "ROD4" of fourth member 104 (FIG. 6).

Second portion 100 further defines a second passage 106 extending through the fourth member 104 and third member 102. Specifically, second passage 106 extends from top surface 104a of fourth member 104 through bottom surface 102b of third member 102. The third member 102 and the fourth member 104 also collectively define a second receiver inner diameter "RID2" for second passage 106 (FIG. 6).

Second portion 100 further includes a plurality of tines 108 extending upwardly from the top surface 102a of third member 102 and disposed adjacent to peripheral edge 102c. Plurality of tines 108 are equidistance space apart from one another along peripheral edge 102c of third member 102. It should be understood that second portion 100 may include any number of plurality of tines 108 and the following description of plurality of tines 108 should equally apply to any number of plurality of tines 108 included with the third member 102 of the second portion 100.

Figure 10:
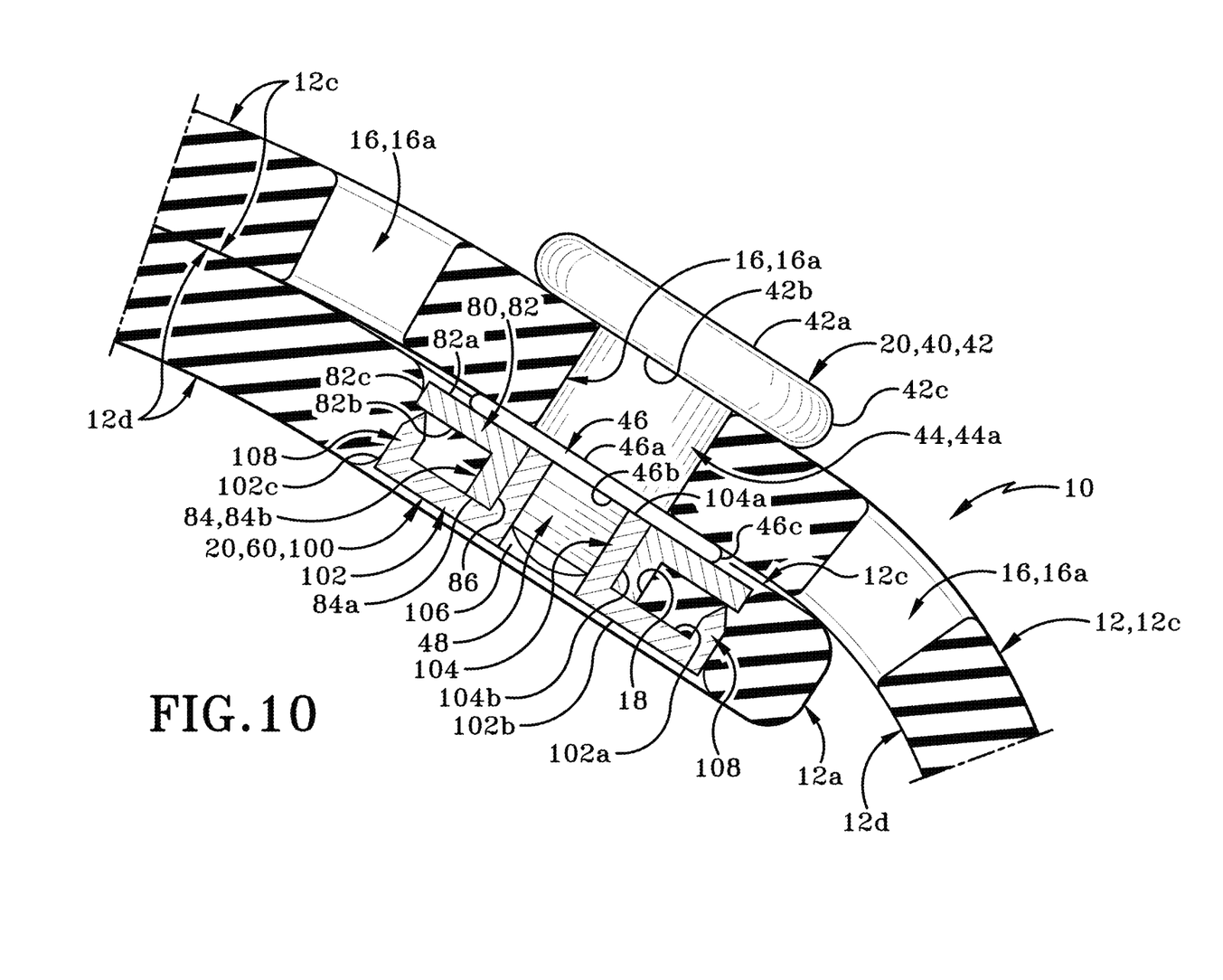
FIG. 10 (FIG. 10) is a partial sectional view of the secured bracelet shown in FIG. 9B depicting the screw fully tightened into the receiver.

Referring now to FIG. 6B, each tine of the plurality of tines 108 generally defines a pentagonal shape when viewed from a sectional view (see FIG. 10). Each tine of the plurality of tines 108 includes a first face 108a and a second face 108b opposite and substantially parallel to one another. First face 108a is continuous with and extending outwardly from peripheral edge 102c of third member 102. Plurality of tines 108 further includes a third face 108c and a fourth face 108d opposite and substantially parallel to one another. Third face 108c and fourth face 108d are continuous and substantially perpendicular to first face 108a and second face 108b. Plurality of tines 108 even further includes a fifth face 108e and a sixth face 108f opposite one another and continuous with first face 108a, second face 108b, third face 108c, and fourth face 108d. Fifth face 108e and sixth face 108f are integrally engaged and define a tip 108g at the connection.

In one specific embodiment, second portion 100 includes six tines 108 spaced equidistant apart from one another along the peripheral edge 102c of third member 102. In other exemplary embodiments, second portion 100 may include any suitable number of tines that are space apart at any suitable distance relative to one another as dictated by the implementation of said tines. In other exemplary embodiments, each tine of a plurality of tines discussed herein may also define a suitable cross-sectional shape.

Referring to FIGS. 6 and 6A, receiver 60 fixedly engages body 12 of bracelet 10. Specifically, receiver 60 is fixedly engages with the body 12 of bracelet 10 within receiver hole 18. First portion 80 of receiver 60 operably engages the body 12 where bottom surface 82b of first member 82 is contiguous with outer surface 12c of body 12 and second member 84 is contiguous with the body 12 inside of receiver hole 18. Second portion 100 of receiver 60 engages the body 12 where top surface 102a of third member 102 is contiguous with inner surface 12d of body 12. Second portion 100 of receiver 60 further engages the body 12 where the plurality of tines 108 penetrate into the body 12 external to the receiver hole 18. With such configuration, the receiver 60 captures a portion of the body 12 based on the clamping configuration performed by the first portion 80 and the second portion 100 inside of and external to the receiver hole 18. Once the receiver 60 is clamped onto the body 12 inside of receiver hole 8, a thickness "T2" of the receiver 60 defined as the distance between top surface 82a of first member 82 of first portion 80 and bottom surface 102b of third member 102 of second portion 100. The thickness "T2" of the receiver 60 is less than the thickness "T" of body 12 of bracelet 10.

Still referring to FIGS. 6 and 6A, tip 108g of plurality of tines 108 extend into body 12 where the tip 108g is contiguous with bottom surface 82b of first member 82. Furthermore, outer surface 104b of fourth member 104 of second portion 100 is contiguous with first passage 86 of first portion 80. Even furthermore, bottom surface 84a of second member 84 of first portion 80 is contiguous with top surface 102a of third member 102 of second portion 100. Lastly, top surface 104a of fourth member 104 of second portion 100 is substantially aligned with top surface 82a of first member 82 of first portion 80.

In one specific embodiment, the second outer diameter "OD2" of the first member 82 of first portion 80 is substantially equal to fourth outer diameter "OD4" of the fourth member 104 of second portion 100. Further in this specific embodiment, the first inner diameter "ID1" of the first passage 86 of the first portion 80 is slightly greater than the fifth outer diameter "OD5" of the fourth member 104 of the second portion 100 wherein the fourth member 104 of the second portion 100 may be received within the first passage 86 of the first member 82.

Referring now to FIG. 10, the locking mechanism 20 is depicted comprising screw 40 fully tightened into the receiver 60. Screw 40 and receiver 60 are operably engaged with one another and the relationship between screw 40 and receiver 60 is depicted more fully below.

When screw 40 is fully tightened into receiver 60, second shaft 48 of screw 40 is disposed within second passage 106 of the second portion 100 of receiver 60. Furthermore, bottom surface 46b of screw 40 is contiguous with top surface 82a of the first portion 80 of receiver 60. Even furthermore, fourth screw outer diameter "SOD4" of the second shaft 48 of the screw 40 is slightly less than the second receiver inner diameter "RID2" of second passage 106 of second portion 100 of receiver 60 wherein the second shaft 48 may be disposed within the second passage 106 of second portion 100 of receiver 60.

Having now described bracelet 10, a method of securing bracelet 10 on a portion of a wearer will now be described in greater detail.

Figure 7:
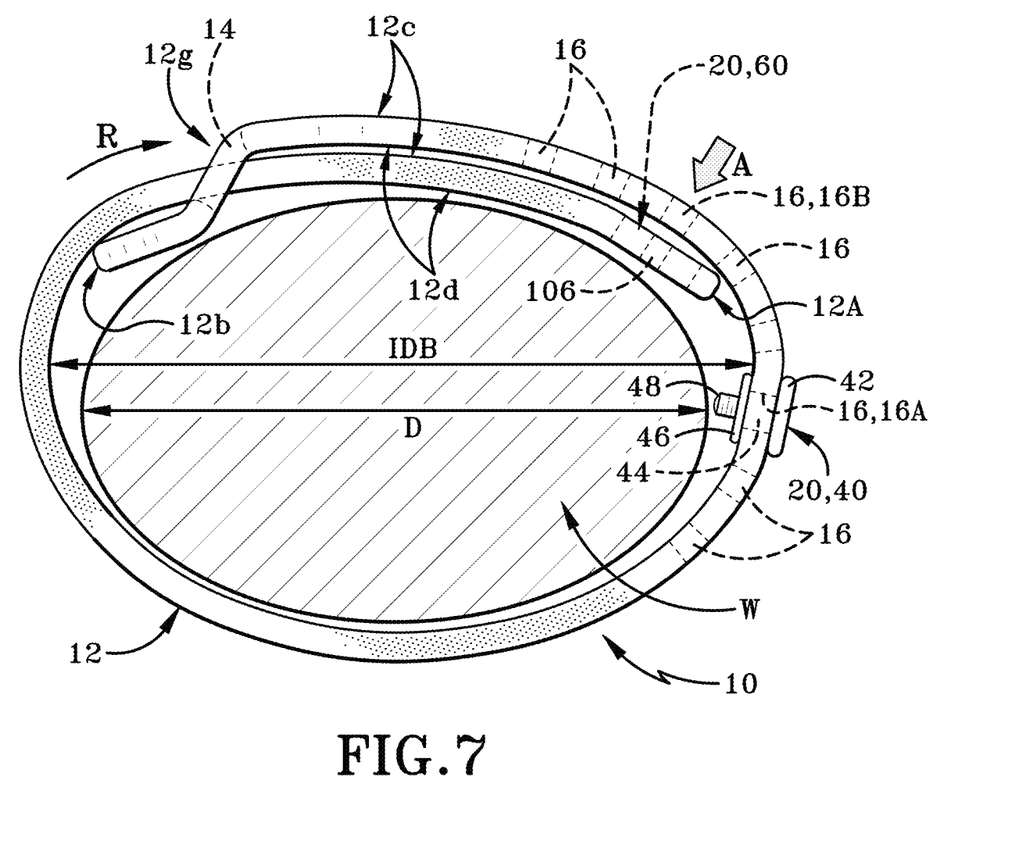
FIG. 7 (FIG. 7) is an operational view of the bracelet being place on a extremity of a human.

Referring now to FIG. 7, a user may place the body 12 of the bracelet 10 about the wearer's extremity "W" by inserting the first end 12*a* of the body 12 of the bracelet 10 into the rectangular bore 14 of the body 12 in the direction of arrow "R" wherein the outer surface 12*c* of the body 12 near the first end 12*a* is disposed below the inner surface 12*d* of the body 12 near the plurality of screw holes 16. The user may then determine and select one of the plurality of screw holes 16 to insert the screw 40 to define a second inner diameter "IDB" of the bracelet 10, generally indicated at arrow "A". The second inner diameter "IDB" of the bracelet 10 may substantially match a diameter "D" of a wearer's extremity "W" so that the bracelet 10 is maintained on the extremity.

Figure 8A:
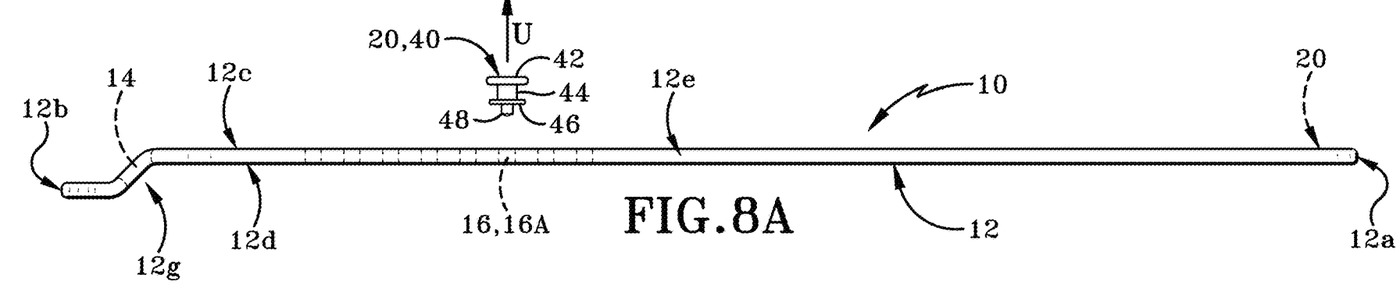
FIG. 8A (FIG. 8A) is an operational view of a screw of the locking mechanism being removed from a hole of a plurality of screw holes of the bracelet.
Figure 8B:
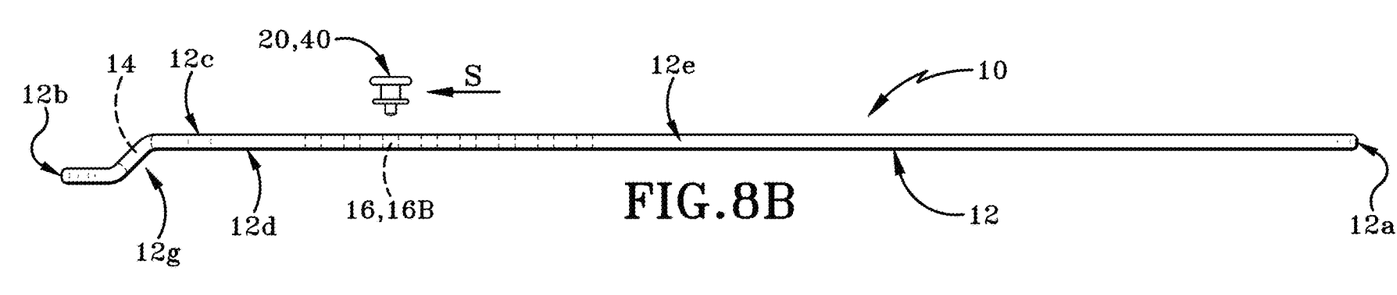
FIG. 8B (FIG. 8B) is another operational view similar to FIG. 8A, but the screw is moved along a body of the bracelet.
Figure 8C:
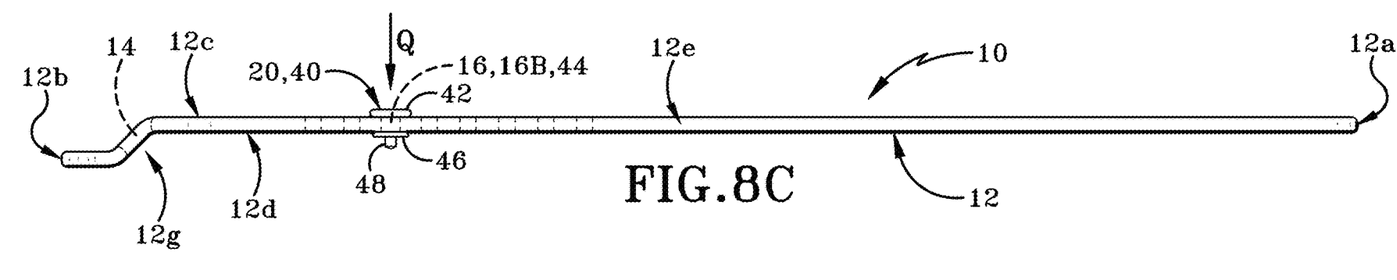
FIG. 8C (FIG. 8C) is another operational view similar to FIG. 8B, but the screw is installed into another hole of the plurality of screw holes of the bracelet.

Referring now to FIGS. 8A, 8B & 8C, the user may place the screw 40 into any one of the plurality of screw holes 16 by removing the screw 40 from a first one of the plurality of screw holes 16A in the direction of arrow "U" (FIG. 8A). Once the screw 40 is removed, the user may then move the screw 40 along the body 12 of the bracelet 10 (arrow "S" in FIG. 8B) until the screw 40 is positioned above a second one of the plurality of screw holes or a desired one of the plurality of screw holes 16B. Once above the desired hole of the plurality of screw holes 16B, the user may then push down in the direction of arrow "Q" (FIG. 8C) to insert the screw 40 into the second one of the plurality of screw holes 16B. The screw 40 is fully seated and engaged with the body 12 when the first flange 42 and the second flange 46 capture and engage with the outer surface 12*c* and the inner surface 12*d* of the body 12.

Figure 9A:
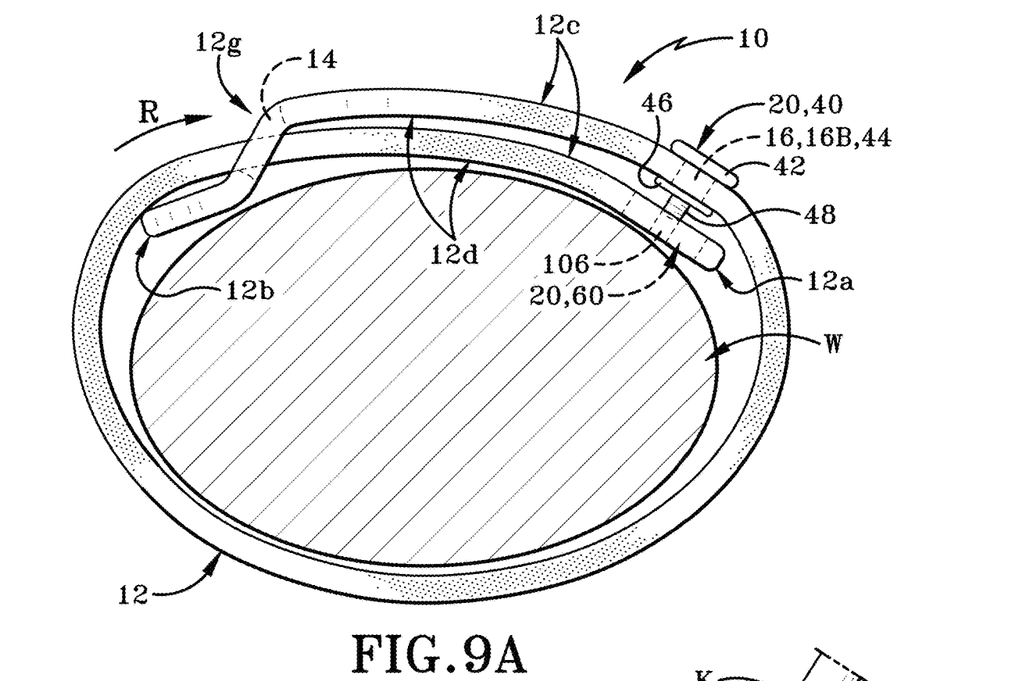
FIG. 9A (FIG. 9A) is an operational view of the bracelet being placed on the extremity of the human and aligning the screw with the receiver.

Once the screw 40 is placed in the second one of the plurality of screw holes 16B, the user may install the bracelet 10 onto the wearer's extremity "W". As best seen in FIG. 9A, the user inserts the first end 12*a* of the body 12 of the bracelet 10 and the receiver 60 into the rectangular bore 14 of the body 12 in the direction of arrow "R" wherein the outer surface 12*c* of the body 12 near the first end 12*a* is disposed below the inner surface 12*d* of the body 12 near the plurality of screw holes 16. The user then guides the receiver 60 along the inner surface 12*d* of body 12 of bracelet 10. It should be understood that while we describe bracelet 10 being placed around a wearer's extremity it should be understood that bracelet 10 may be placed on any number of items such as a human's wrist, a human's ankle, or an animal.

Figure 9B:
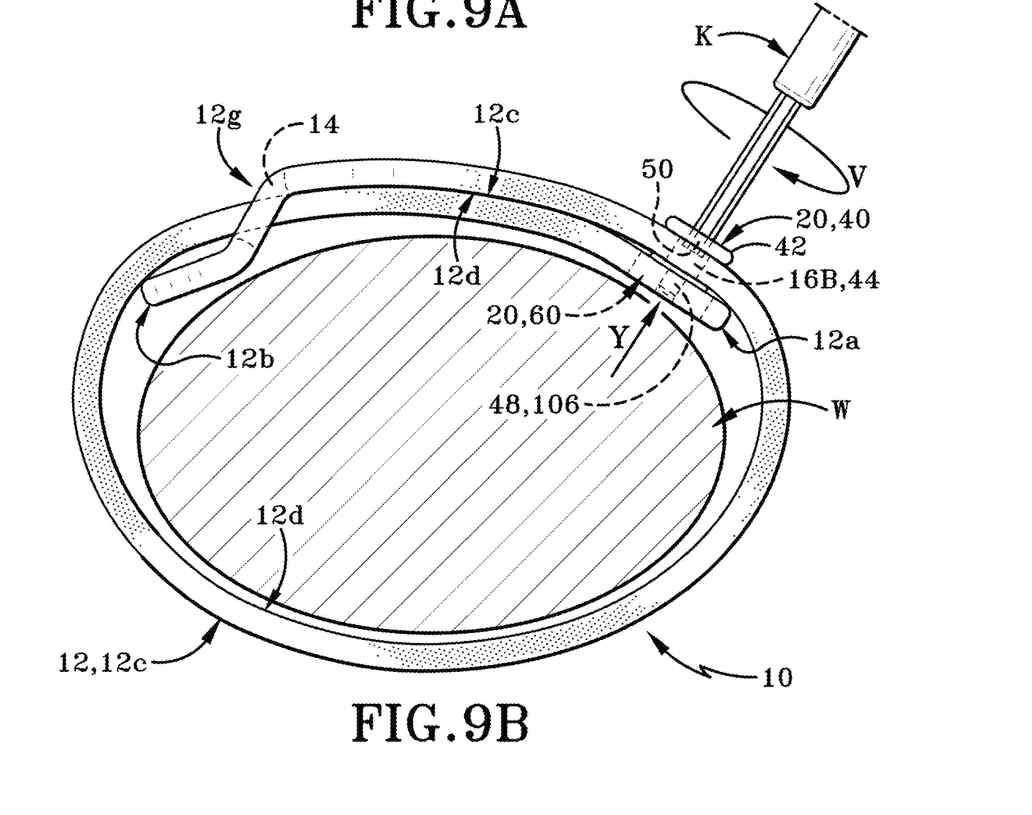
FIG. 9B (FIG. 9B) is another operational view of securing the bracelet shown in FIG. 9A by tightening the screw into the receiver by an external tool.

Once the first end 12*a* and receiver 60 pass through the rectangular bore 14, the user may then align the screw 40 with the receiver 60 to secure the bracelet 10 to the wearer's extremity. Referring now to FIG. 9B, the user then secures the bracelet 10 about the wearer's extremity "W" by inserting external tool "K" into the socket 50 of the screw 40 and tightening the screw 40 into the receiver 60 in the direction of arrow "V". As the screw 40 is tightened into the receiver 60, the outer surface 12*c* of the body 12 near the plurality of screw holes 16 of the body 12 is pulled closer to the inner surface 12*d* of the body 12 near the first end 12*a* in the direction of arrow "Y". Once the screw 40 is fully tightened, the outer surface 12*c* of the body 12 near the plurality of screw holes 16 is contiguous with the inner surface 12*d* of the body 12 near the plurality of screw holes 16.

Having now described bracelet 10 and the method of securing bracelet 10 on a portion of a wearer, a method for protecting an at risk individual, will now be described in greater detail.

The user or another person places the bracelet 10 around the extremity of the at risk individual. The user or another person secures the bracelet around the extremity of the at risk individual with an locking mechanism 20 so that the bracelet 10 cannot be removed without an external tool "K." The user or another person puts indicia on the bracelet relating to the at risk individual wearing the bracelet.

In one specific embodiment, the indicia may be on the outer surface 12*c* of the bracelet 10. Further in this specific embodiment, the indicia include at least one of health information, personal information, contact information and combinations thereof.

In another specific embodiment, the at risk individual may be one of a child, a physically hurt person, a lost person, a mentally challenged individual, a physically challenged individual or any combination thereof.

In yet another specific embodiment, the method for protecting an at risk individual may further comprise the steps of a bystander finding the at risk individual. The bystander the locating the bracelet 10 on the at risk individual and the bystander reading the information on the indicia on the bracelet 10. After locating the needed information on the indicia, the bystander may procure help for the wearer in need of help.

Unless explicitly stated that a particular shape or configuration of a component is mandatory, any of the elements, components, or structures discussed herein may take the form of any shape. Thus, although the figures depict the various elements, components, or structures of the present disclosure according to one or more exemplary embodiments, it is to be understood that any other geometric configuration of that element, component, or structure is entirely possible. For example, instead of the plurality of tines 108 being pentagonal in shaft, the plurality of tines 108 can be semi-circular triangular, rectangular or square, pentagonal, hexagonal, heptagonal, octagonal, decagonal, dodecagonal, diamond shaped or another parallelogram, trapezoidal, star-shaped, oval, ovoid, lines or lined, teardrop-shaped, cross-shaped, donut-shaped, heart-shaped, arrow-shaped, crescent-shaped, any letter shape (i.e., A-shaped, B-shaped, C-shaped, D-shaped, E-shaped, F-shaped, G-shaped, H-shaped, I-shaped, J-shaped, K-shaped, L-shaped, M-shaped, N-shaped, O-shaped, P-shaped, Q-shaped, R-shaped, S-shaped, T-shaped, U-shaped, V-shaped, W-shaped, X-shaped, Y-shaped, or Z-shaped), or any other type of regular or irregular, symmetrical or asymmetrical configuration.

Various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

While components of the present disclosure are described herein in relation to each other, it is possible for one of the components disclosed herein to include inventive subject matter, if claimed alone or used alone. In keeping with the above example, if the disclosed embodiments teach the features of A and B, then there may be inventive subject matter in the combination of A and B, A alone, or B alone, unless otherwise stated herein.

As used herein in the specification and in the claims, the term "effecting" or a phrase or claim element beginning with the term "effecting" should be understood to mean to cause something to happen or to bring something about. For example, effecting an event to occur may be caused by actions of a first party even though a second party actually performed the event or had the event occur to the second party. Stated otherwise, effecting refers to one party giving another party the tools, objects, or resources to cause an event to occur. Thus, in this example a claim element of "effecting an event to occur" would mean that a first party is giving a second party the tools or resources needed for the second party to perform the event, however the affirmative single action is the responsibility of the first party to provide the tools or resources to cause said event to occur.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Spatially relative terms, such as "under", "below", "lower", "over", "upper", "above", "behind", "in front of", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal", "lateral", "transverse", "longitudinal", and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed herein could be termed a second feature/element, and similarly, a second feature/element discussed herein could be termed a first feature/element without departing from the teachings of the present invention.

An embodiment is an implementation or example of the present disclosure. Reference in the specification to "an embodiment," "one embodiment," "some embodiments," "one particular embodiment," "an exemplary embodiment," or "other embodiments," or the like, means that a particular feature, structure, or characteristic described in connection with the embodiments is included in at least some embodiments, but not necessarily all embodiments, of the invention. The various appearances "an embodiment," "one embodiment," "some embodiments," "one particular embodiment," "an exemplary embodiment," or "other embodiments," or the like, are not necessarily all referring to the same embodiments.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Additionally, the method of performing the present disclosure may occur in a sequence different than those described herein. Accordingly, no sequence of the method should be read as a limitation unless explicitly stated. It is recognizable that performing some of the steps of the method in a different order could achieve a similar result.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

To the extent that the present disclosure has utilized the term "invention" in various titles or sections of this specification, this term was included as required by the formatting requirements of word document submissions pursuant the guidelines/requirements of the United States Patent and Trademark Office and shall not, in any manner, be considered a disavowal of any subject matter.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

What is claimed is:

1. An identification bracelet, said bracelet comprising:
   a body having a first end and a second end opposite to the first end;
   a receiver hole defined in the body at the first end;
   a plurality of screw holes defined in the body at a location between the first end and the second end and is remote from the receiver hole;
   a locking mechanism fixedly engaged with the body at the receiver hole and selectively operably engageable with the body at a selected hole of the plurality of screw holes;
   wherein the locking mechanism comprises:
      a screw selectively operably engageable with the body at the selected hole of the plurality of screw holes and a receiver fixedly engaged with the body at the receiver hole and is configured to receive the screw;
   wherein the screw comprises:
      a first flange selectively operably engageable with an outer surface of the body;
      a first shaft operably engaged with the first flange and is selectively operably engageable with an inner wall of the selected hole of the plurality of screw holes;
      a second flange operably engaged with the first shaft and is selectively operably engageable an inner surface of the body;
   a second shaft operably engaged with the second flange and is selectively operably engageable with the receiver;
   an socket defined in the first flange and the first shaft;
   wherein the socket is adapted to receive an external tool for securing the screw with the receiver; and.

2. The bracelet of claim 1, wherein the body of the bracelet comprises:
   an outer surface and an inner surface opposite to the outer surface;
   an indicia on the outer surface of the body of the bracelet; and
   wherein the indicia includes at least one of health information, personal information, contact information and combinations thereof.

3. The bracelet of claim 1, wherein the body of the bracelet comprises:
a bore defined at the second end; and
wherein the bore is configured to receive the first end of the body.

4. The bracelet of claim 3, wherein the body of the bracelet further comprises:
an outer surface and an inner surface opposite one another;
a first side and a second side opposite one another and positioned between the outer surface and the inner surface; and
wherein each of the receiver hole and the plurality of screw holes extends through the outer surface and the inner surface.

5. The bracelet of claim 1, wherein the external tool is a hex key.

6. The bracelet of claim 1, wherein the receiver comprises:
a first portion and a second portion configured to engage with one another; and
wherein the first portion and the second portion are configured to fixedly engage with the body of the bracelet inside of the receiver hole.

7. An identification bracelet, said bracelet comprising:
a body having a first end and a second end opposite to the first end;
a receiver hole defined in the body at the first end;
a plurality of screw holes defined in the body at a location between the first end and the second end and is remote from the receiver hole;
a locking mechanism fixedly engaged with the body at the receiver hole and selectively operably engageable with the body at a selected hole of the plurality of screw holes;
wherein the locking mechanism comprises:
a screw selectively operably engageable with the body at the selected hole of the plurality of screw holes;
a receiver fixedly engaged with the body at the receiver hole and is configured to receive the screw;
wherein the receiver comprises:
a first portion comprising:
a first member operably engaged with an outer surface of the body;
a second member integrally engaged with the first member and is operably engaged with the receiver hole of the body;
a first passage extending between the first member and the second member;
a second portion comprising:
a third member operably engaged with to an inner surface of the body;
a fourth member integrally engaged with the third member and is configured to be received within the receiver hole of the body;
a second passage extending between the third member and the fourth member;
a plurality of tines extending outwardly from the third member and engaged with the third member;
wherein the fourth member of the second portion is configured to be received within first passage of the first portion; and
wherein the second passage is configured to receive the screw.

8. The bracelet of claim 7, wherein the first portion and the second portion define outer diameters substantially equal to one another.

9. The bracelet of claim 7, wherein a wall of the fourth member of the second portion is contiguous with the first passage of the first portion.

10. The bracelet of claim 7, wherein a top surface of the fourth member of the second member is substantially aligned with a top surface of the first member of the first portion.

11. The bracelet of claim 7, wherein a tip of each of the plurality of tines is contiguous with a bottom surface of the first member of the first portion of the receiver.

12. The bracelet of claim 7, wherein the receiver further comprises the second passage configured to receive a second shaft of the screw; and wherein the second passage of the second portion and the second shaft of the screw are threaded.

13. The bracelet of claim 7, wherein the body of the bracelet comprises:
an outer surface and an inner surface opposite to the outer surface;
an indicia on the outer surface of the body of the bracelet; and
wherein the indicia includes at least one of health information, personal information, contact information and combinations thereof.

14. The bracelet of claim 7, wherein the body of the bracelet comprises:
a bore defined at the second end; and
wherein the bore is configured to receive the first end of the body.

15. A method of securing an identification bracelet to an extremity of a wearer, comprising steps of:
placing a body of the bracelet around the extremity of the wearer;
inserting a first end of the body of the bracelet into a bore of the body;
guiding a receiver of a locking mechanism along an inner surface of the body of the bracelet;
aligning the receiver with a screw of the locking mechanism;
tightening the screw into the receiver; and
securing the bracelet to the extremity of the wearer.

16. The method according to claim 15, further comprising steps of:
wrapping the body of the bracelet about the extremity of the wearer;
determining a second inner diameter of the body of the bracelet that substantially matches with an outer diameter of the extremity;
selecting a desired hole of the plurality of screw holes that sets the second inner diameter of the body; and
placing the screw into the desired hole of the plurality of screw holes.

17. The method according to claim 16, wherein placing the screw into the desired hole of the plurality of screw holes further comprises:
pushing the screw downwardly to insert the screw into the desired hole of the plurality of screw holes.

18. The method according to claim 16, wherein the step of tightening the screw into the receiver further includes that the screw is tightened into the receiver with an external tool separate from the bracelet.

19. The method according to claim 15, wherein tightening the screw into the receiver further comprises:

pulling an outer surface of body proximate the plurality of screw holes closer to an inner surface of the body proximate the first end of the body.

20. The method according to claim 15, wherein after the screw is tighten into the receiver an outer surface of body proximate the plurality of screw holes is contiguous with an inner surface of the body proximate the first end of the body.

* * * * *